(12) United States Patent
Ranucci et al.

(10) Patent No.: US 12,048,424 B2
(45) Date of Patent: *Jul. 30, 2024

(54) ACTUATION LOCKOUT FOR A SURGICAL INSTRUMENT

(71) Applicant: C.R. Bard, Inc., Murray Hill, NJ (US)

(72) Inventors: Kevin J. Ranucci, Warwick, RI (US); Nathan Stewart Cauldwell, Hope, RI (US); Donald E. Ziniti, Cumberland, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 42 days.

This patent is subject to a terminal disclaimer.

(21) Appl. No.: 17/848,497

(22) Filed: Jun. 24, 2022

(65) Prior Publication Data

US 2022/0313228 A1 Oct. 6, 2022

Related U.S. Application Data

(60) Continuation of application No. 16/992,290, filed on Aug. 13, 2020, now Pat. No. 11,389,143, which is a (Continued)

(51) Int. Cl.
*A61B 17/072* (2006.01)
*A61B 17/00* (2006.01)
(Continued)

(52) U.S. Cl.
CPC .......... *A61B 17/00* (2013.01); *A61B 17/0469* (2013.01); *A61B 17/068* (2013.01);
(Continued)

(58) Field of Classification Search
CPC ................ A61B 17/068; A61B 17/072; A61B 17/07207; A61B 17/115; A61B 17/00234;
(Continued)

(56) References Cited

U.S. PATENT DOCUMENTS 5,665,105 A 9/1997 Furnish et al.
5,762,255 A 6/1998 Chrisman et al.
(Continued)

FOREIGN PATENT DOCUMENTS

CN 1717198 A 1/2006
CN 102271596 A 12/2011
(Continued)

OTHER PUBLICATIONS

International Search Report and Written Opinion for Application No. PCT/US2016/028585, mailed Jul. 26, 2016.

*Primary Examiner* — Scott A Smith
(74) *Attorney, Agent, or Firm* — Wolf, Greenfield & Sacks, P.C.

(57) ABSTRACT

Embodiments of a surgical instrument including an actuation lockout system as well as its method of use are disclosed. In one embodiment, a surgical instrument includes a trigger and a driveshaft coupled to the trigger such that actuation of the trigger causes the driveshaft to move from a first position to a second position, thereby resulting in deployment of a surgical fastener. An actuation lockout system restrains distal movement of the driveshaft until a force greater than or equal to a threshold force is applied to the trigger.

21 Claims, 5 Drawing Sheets

Related U.S. Application Data continuation of application No. 16/180,435, filed on Nov. 5, 2018, now Pat. No. 10,772,613, which is a division of application No. 14/711,324, filed on May 13, 2015, now Pat. No. 10,159,471.

(51) Int. Cl.
*A61B 17/04* (2006.01)
*A61B 17/068* (2006.01)
*A61B 17/10* (2006.01)
*A61B 17/32* (2006.01)
*A61B 90/00* (2016.01)
*A61B 17/29* (2006.01)

(52) U.S. Cl.
CPC ...... *A61B 17/072* (2013.01); *A61B 17/07207* (2013.01); *A61B 17/10* (2013.01); *A61B 17/32* (2013.01); *A61B 90/03* (2016.02); *A61B 2017/00367* (2013.01); *A61B 2017/00398* (2013.01); *A61B 2017/07214* (2013.01); *A61B 2017/2912* (2013.01); *A61B 2017/2929* (2013.01); *A61B 2017/293* (2013.01); *A61B 2017/2946* (2013.01); *A61B 2090/0807* (2016.02)

(58) Field of Classification Search
CPC ........... A61B 2017/07214; A61B 2017/00367; A61B 2017/00398; A61B 2017/2912; A61B 2017/2919; A61B 2017/2923; A61B 2017/2946; A61B 2090/0807
USPC ..... 227/19, 175.1, 175.2, 176.1; 606/1, 139, 606/219
See application file for complete search history.

(56) References Cited

U.S. PATENT DOCUMENTS

| | | | |
|---|---|---|---|
| 5,827,263 | A | 10/1998 | Furnish et al. |
| 6,042,601 | A | 3/2000 | Smith |
| 6,053,388 | A | 4/2000 | Pfister et al. |
| 6,457,625 | B1 | 1/2002 | Toermaelae et al. |
| 6,425,900 | B1 | 7/2002 | Knodel et al. |
| 7,143,926 | B2 | 12/2006 | Shelton et al. |
| 7,481,347 | B2 | 1/2009 | Roy |
| 7,485,124 | B2 | 2/2009 | Kuhns et al. |
| 7,540,400 | B2 | 6/2009 | Zins et al. |
| 7,569,063 | B2 | 8/2009 | Bailly et al. |
| 7,694,863 | B2 | 4/2010 | Spasov et al. |
| 7,740,159 | B2 | 6/2010 | Shelton et al. |
| 7,771,440 | B2 | 10/2010 | Ortiz et al. |
| 7,832,612 | B2 | 11/2010 | Baxter, III et al. |
| 7,886,953 | B2 | 2/2011 | Schwemberger |
| 7,931,660 | B2 | 4/2011 | Aranyi et al. |
| 8,403,944 | B2 | 3/2013 | Pain et al. |
| 8,424,737 | B2 | 4/2013 | Scirica |
| 8,684,247 | B2 | 1/2014 | Scirica et al. |
| 8,683,895 | B2 | 4/2014 | Nash |
| 8,794,496 | B2 | 5/2014 | Scirica |
| 9,089,379 | B2 | 7/2015 | Sack et al. |
| 9,364,235 | B2 | 6/2016 | Ranucci et al. |
| 9,526,498 | B2 | 12/2016 | Reed |
| 10,159,481 | B2 | 5/2018 | Whitman et al. |
| 10,159,471 | B2 | 12/2018 | Ranucci et al. |
| 10,772,613 | B2 | 9/2020 | Ranucci et al. |
| 11,389,143 | B2 | 7/2022 | Ranucci et al. |
| 2006/0085019 | A1 | 4/2006 | Cote et al. |
| 2008/0029576 | A1 | 2/2008 | Shelton et al. |
| 2009/0236395 | A1 | 9/2009 | Scirica |
| 2009/0312603 | A1 | 12/2009 | Lam et al. |
| 2011/0130782 | A1 | 2/2011 | Kan et al. |
| 2011/0079627 | A1 | 4/2011 | Cardinale et al. |
| 2012/0283739 | A1 | 8/2012 | Ralph et al. |
| 2013/0116710 | A1 | 9/2013 | Ziniti et al. |
| 2014/0326249 | A1 | 6/2014 | Cappiello et al. |
| 2014/0263544 | A1 | 9/2014 | Ranucci et al. |
| 2014/0276963 | A1 | 9/2014 | Ranucci et al. |
| 2015/0150558 | A1 | 4/2015 | Zergiebel |
| 2016/0331462 | A1 | 11/2016 | Ranucci et al. |
| 2019/0069888 | A1 | 3/2019 | Ranucci et al. |
| 2020/0367869 | A1* | 11/2020 | Ranucci ................ A61B 17/32 |

FOREIGN PATENT DOCUMENTS

| | | |
|---|---|---|
| CN | 103349560 A | 10/2013 |
| CN | 103989497 A | 8/2014 |
| CN | 104042278 A | 9/2014 |
| CN | 104042281 A | 9/2014 |
| CN | 203970461 U | 12/2014 |
| CN | 104414740 A | 3/2015 |
| JP | 2004-147701 A | 5/2004 |
| JP | 2008-188425 A | 8/2008 |
| JP | 2009-34491 A | 2/2009 |
| JP | 2015-16347 A | 1/2015 |
| JP | 2015-61607 A | 4/2015 |
| JP | 2016-508414 A | 3/2016 |
| WO | WO 2011/044343 A2 | 4/2011 |
| WO | WO 2014/124008 A1 | 8/2014 |
| WO | WO 2014/133772 A1 | 9/2014 |
| WO | WO 2016/000255 A1 | 1/2016 |

* cited by examiner

ACTUATION LOCKOUT FOR A SURGICAL INSTRUMENT

RELATED APPLICATIONS

This application is a continuation of U.S. application Ser. No. 16/992,290, filed Aug. 13, 2020, now U.S. Pat. No. 11,389,143, which is a continuation of U.S. application Ser. No. 16/180,435, filed Nov. 5, 2018, now U.S. Pat. No. 10,772,613, which is a divisional of U.S. application Ser. No. 14/711,324, filed May 13, 2015, the disclosures now U.S. Pat. No. 10,159,471, of each of which are incorporated by reference herein in their entirety.

FIELD

Disclosed embodiments are related to actuation lockouts for surgical instruments.

BACKGROUND

Oftentimes a surgical mesh fabric or other prosthetic repair fabric is used during a surgical repair of a hernia or other tissue defect. The prosthetic repair fabric may be placed in an open procedure or laparoscopically. To secure the repair fabric in place, one or more fasteners may be deployed through the prosthetic repair fabric and into the underlying tissue.

SUMMARY

In one embodiment, a surgical instrument includes a power transmission including a trigger and a driveshaft operatively coupled to the trigger. Actuation of the trigger moves the driveshaft between at least a first position and a second position. The surgical instrument further includes an actuation lockout system operatively associated with the power transmission. The actuation lockout system substantially prevents movement of the driveshaft from the first position to the second position until a force greater than or equal to a threshold force is applied to the trigger.

In another embodiment, a surgical instrument includes a power transmission including and a driveshaft operatively coupled to the trigger. Actuation of the trigger moves the driveshaft between at least a first position and a second position. The surgical instrument further includes a first camming surface associated with a portion of the power transmission and a second camming surface arranged to block movement of the first camming surface in a locked configuration, and permit movement of the first camming surface in an unlocked configuration. A biasing member is operatively coupled to at least one of the first camming surface and second camming surface. The biasing member urges the camming surfaces into the locked configuration. An actuation force greater than or equal to a threshold force applied to the trigger moves the first camming surface and the second camming surface to the unlocked configuration.

In yet another embodiment, a method of operating a surgical instrument includes initially restraining movement of a driveshaft operatively associated with a trigger using an actuation lockout system. The method further includes applying a force greater than or equal to a threshold force to a trigger of the surgical instrument to move an actuation lockout system from a locked configuration to an unlocked configuration, and displacing the driveshaft from a first position to a second position when the actuation lockout system is in the unlocked configuration.

It should be appreciated that the foregoing concepts, and additional concepts discussed below, may be arranged in any suitable combination, as the present disclosure is not limited in this respect. Further, other advantages and novel features of the present disclosure can be more fully understood from the following description in conjunction with the accompanying drawings.

In cases where the present specification and a document incorporated by reference include conflicting and/or inconsistent disclosure, the present specification shall control.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

The inventors have recognized issues associated with slow, partial, and/or unintentional actuations of a surgical instrument. Consequently, the inventors have realized the benefits associated with providing an actuation lockout system that restrains actuation of a surgical instrument until a threshold force is applied to an actuation trigger. Without wishing to be bound by theory, in some instances when a user overcomes the threshold force to actuate the surgical instrument, it may result in the user naturally completing a full actuation of the surgical instrument while avoiding a slow, partial, and/or unintentional actuation though other benefits may also result from such an instrument as the disclosure is not so limited.

In some embodiments, a surgical instrument includes a power transmission including a trigger operatively coupled to a drive shaft. The power transmission transfers force applied to the trigger by a user to the driveshaft which is constructed and arranged to deploy a fastener from a distal end of the surgical instrument. The surgical instrument may also include an actuation lockout system associated with any portion of the power transmission including the trigger, driveshaft, and/or any intermediate component to prevent actuation of the surgical instrument until a threshold force is applied to the trigger. Components that may be included in a power transmission between the trigger and driveshaft include spur gears, helical gears, crown gears, worm gears, planetary gear systems, belts, clutch interfaces, linkages, or any other appropriate component capable of transmitting power from one component to another. However, embodiments in which the trigger is directly coupled to the driveshaft are also contemplated. Further, it should be understood that the driveshaft may be configured to deploy any appropriate type of fastener including both linearly or rotationally deployed fasteners. Consequently, it should be understood that the power transmission and driveshaft may provide a linear or rotational force to an associated fastener when the trigger is actuated. Various embodiments of specific actuation lockout systems are described in more detail below.

It should be understood that the current disclosure is not limited to any particular displacement direction of the driveshaft. For example, in some embodiments, the driveshaft may be displaced axially, rotationally, or in any other appropriate fashion. Further, the actuation lockout system may be constructed and arranged in any suitable manner to facilitate restraining displacement of the driveshaft in any suitable direction until a force greater than or equal to a threshold force is applied to the trigger.

Depending on the particular embodiment, the threshold force required to transition the actuation lockout system from a locked configuration in which actuation of the surgical instrument is restrained, to an unlocked configuration in which actuation of the surgical instrument is not restrained, may be larger than or equal to a force required to actuate the surgical instrument to deploy a surgical fastener or accomplish another action via actuation of the trigger such as cutting, suturing, as well as staple deployment to name a few. Therefore, application of the threshold force to the trigger and subsequent transitioning of the actuation lockout system from the locked configuration to the unlocked configuration may result in a user naturally completing full actuation of the trigger because they are already applying a force greater than or equal to the actuation force. This may substantially prevent slow and/or incomplete deployment of a surgical fastener when used in a surgical fastening instrument. While the threshold force may be greater than or equal to the actuation force in some embodiments, it should be understood that in other embodiments, the threshold force may be less than or equal to the actuation force as the disclosure is not so limited.

It should be understood that an actuation lockout out may have any appropriate force threshold for actuation. For example, the threshold force may be greater than or equal to about 0.25 pounds, 0.5 pounds, 1 pound, 2 pounds, or any other appropriate force. Correspondingly, the threshold force may be less than or equal to about 5 pounds, 4 pounds, 3 pounds, 2 pounds, 1 pound, or any other appropriate force. Various combinations of the above threshold force limits are contemplated including a threshold force between or equal to about 0.5 pounds to 1 pound, 1 pound to 5 pounds, or any other combination.

Similar to the above, it should be understood that an actuation force for deploying a fastener may be any appropriate force as the disclosure is not so limited. For instance, the actuation force may be greater than or equal to about 0.25 pounds, 0.5 pounds, 1 pound, 2 pounds, or any other appropriate force. Correspondingly, the threshold force may be less than or equal to about 4 pounds, 3 pounds, 2 pounds, 1 pound, or any other appropriate force. Various combinations of the above threshold force limits are contemplated including a threshold force between or equal to about 0.5 pounds to 1 pound, 1 pound to 4 pounds, or any other combination.

In one embodiment, actuation of a driveshaft to deploy a surgical fastener involves moving the driveshaft from a first position to a second position. Depending on whether a linearly or rotationally deployed fastener is used, the driveshaft displacement may involve either a first and second rotational position or a first proximal longitudinal position and a second distal longitudinal position. In either case, an actuation lockout system associated with a power transmission including the driveshaft is configured to restrain movement of the driveshaft from the first position to the second position until a threshold force is applied to a trigger operatively coupled to the driveshaft. During actuation, the actuation lockout system may be transitioned between a locked configuration in which motion of the driveshaft is restrained, and an unlocked configuration in which the driveshaft is permitted to move. The actuation lockout system transitions from the locked configuration to the unlocked configuration when a force greater than or equal to the threshold force is applied to the trigger.

Depending on the embodiment, an actuation lockout system may be moved between locked and unlocked configurations in any number of ways. In one embodiment, an actuation lockout system is movable between the locked and unlocked configuration using a suitable arrangement of two or more corresponding surfaces disposed on various portions of the power transmission and/or surgical instrument. For example, in one embodiment, an actuation lockout system includes a first surface directly, or indirectly, coupled to the driveshaft and a second surface directly, or indirectly, coupled to the handle or other portion of a surgical instrument that is arranged to selectively block movement of the first surface. When the actuation lockout system is in the locked configuration, the second surface is engaged with the first surface such that displacement of the first surface, and therefore the driveshaft, which is operatively coupled to the first surface, is restricted. Correspondingly, when the actuation lockout system is in the unlocked configuration, the first and second surfaces are disengaged, separated, or otherwise configured to allow the first surface, and the associated driveshaft, to freely move relative to the second surface. Specific embodiments of arrangements of the first and second surfaces are detailed further below.

In certain embodiments, engaging surfaces arranged to selectively prevent actuation of a surgical instrument form a camming arrangement such that the surfaces are urged from a locked configuration to an unlocked configuration when a sufficient force is applied to actuate the driveshaft. Such a camming arrangement may be desirable to provide a simple actuation lockout system which automatically moves from the locked configuration to the unlocked configuration during actuation of the driveshaft from a first position to a second position. For example, a first camming surface associated with the driveshaft may be engaged with a second camming surface associated with a handled of a surgical instrument when an actuation lockout system is in a locked configuration. The camming surfaces may be configured such that a force applied to actuate the driveshaft causes the first camming surface to apply a force to the second camming surface that displaces the second camming surface to the unlocked configuration, thereby allowing relative movement of the first and second surfaces and thus actuation of the driveshaft.

The various embodiments of an actuation lockout system disclosed herein are not limited to any particular type of fastener or surgical instrument. For example, an actuation lockout system could be used with a tack, clip, staple, pin, tissue anchor, bone anchor, coil fasteners, screw fasteners, and any other type of fastener that could benefit from the use of an actuation lockout system to avoid incomplete and/or unintentional deployment of a fastener. Similarly, the actuation lockout system may be used in any number of medical procedures including, but not limited to, attaching a repair fabric or mesh to underlying tissue, attaching adjacent layers of tissue, attaching identification devices and/or tags to livestock, and other appropriate applications involving the deployment of a fastener.

For the sake of clarity, the currently disclosed embodiments are directed to laparoscopic fastening devices. However, the current disclosure is not so limited. Instead, the actuation lockout system could be incorporated in any actuated surgical instrument. For example, an actuation lockout system could be employed in an endoscopic device, a borescopic device, a catheter, a surgical instrument for use in "open" procedures, surgical instruments including actuated working tools, or any other appropriate surgical instrument. In embodiments where the surgical instrument deploys fasteners, the surgical instrument may be constructed to allow the user to load the instrument with one or more fasteners, be preloaded with one or more fasteners, be selectively connected with a disposable loading unit including one or more preloaded fasteners, or be constructed in any other appropriate manner.

Turning now to the figures, specific non-limiting embodiments of actuation lockout systems and surgical instruments are described.

Figure 1:
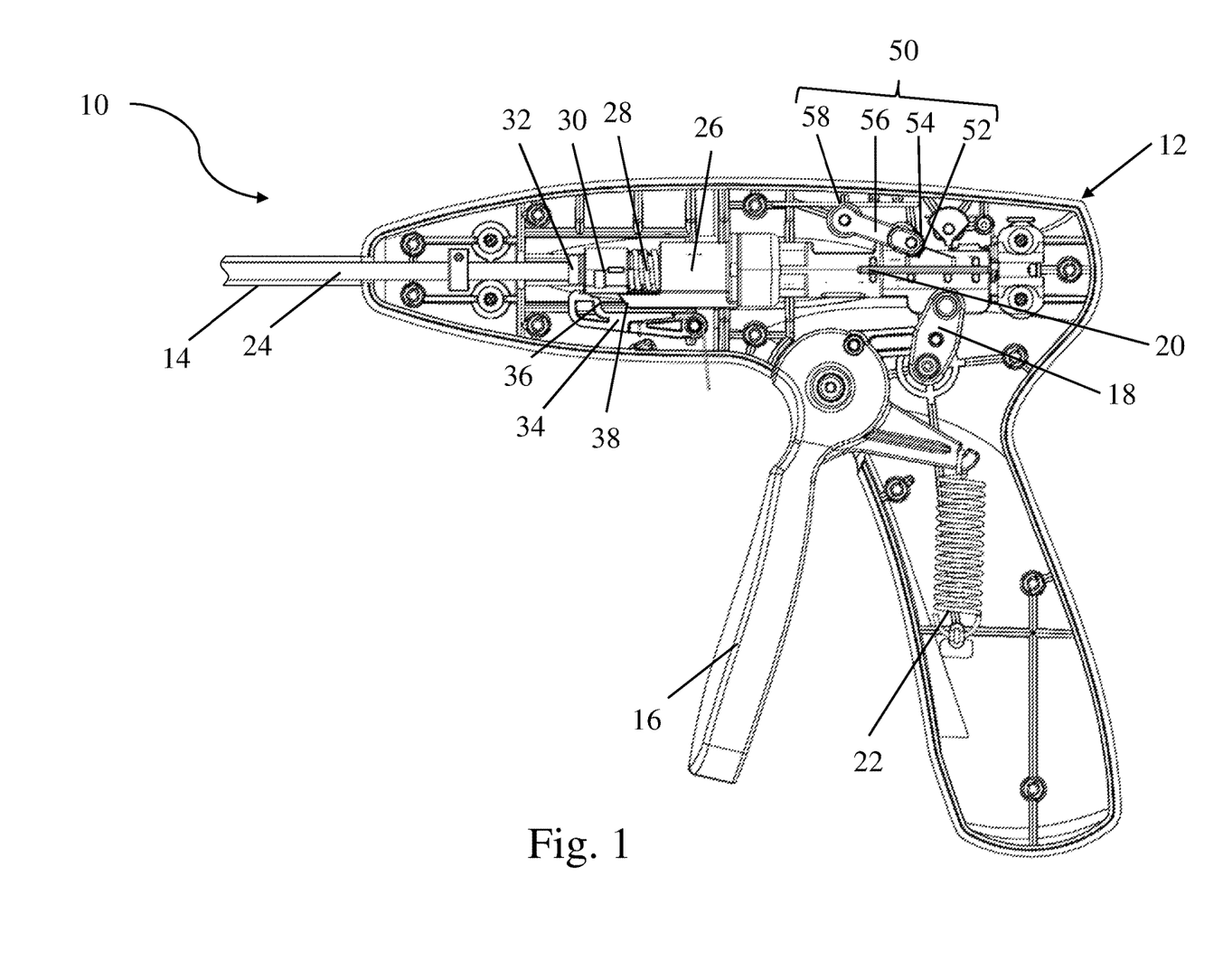
FIG. 1 is a cross-sectional view of a surgical instrument incorporating an actuation lockout system.
Figure 2:
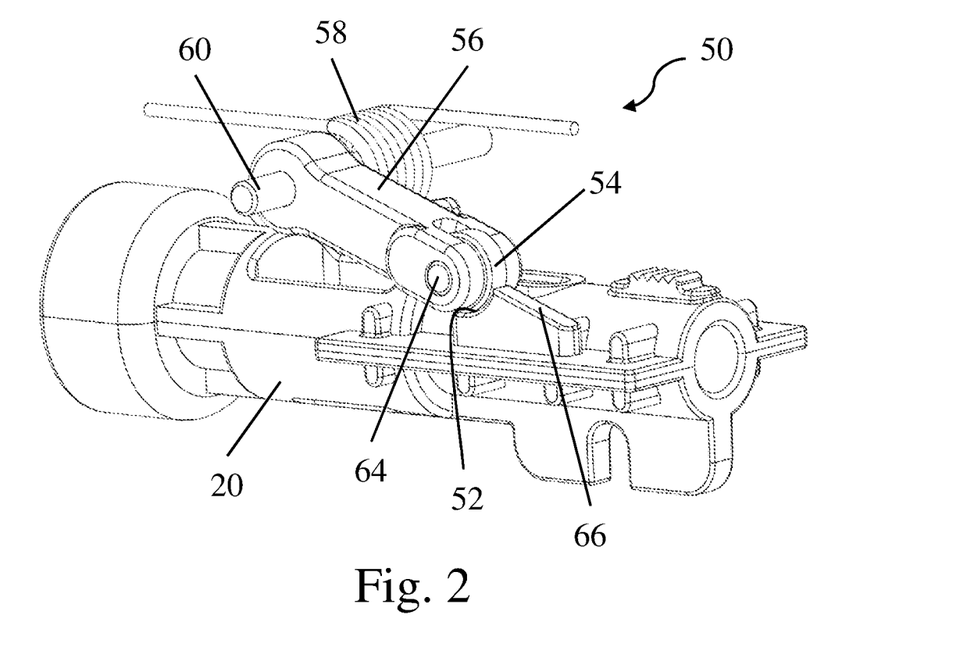
FIG. 2 is a perspective view of one embodiment of an actuation lockout system.
Figure 3:
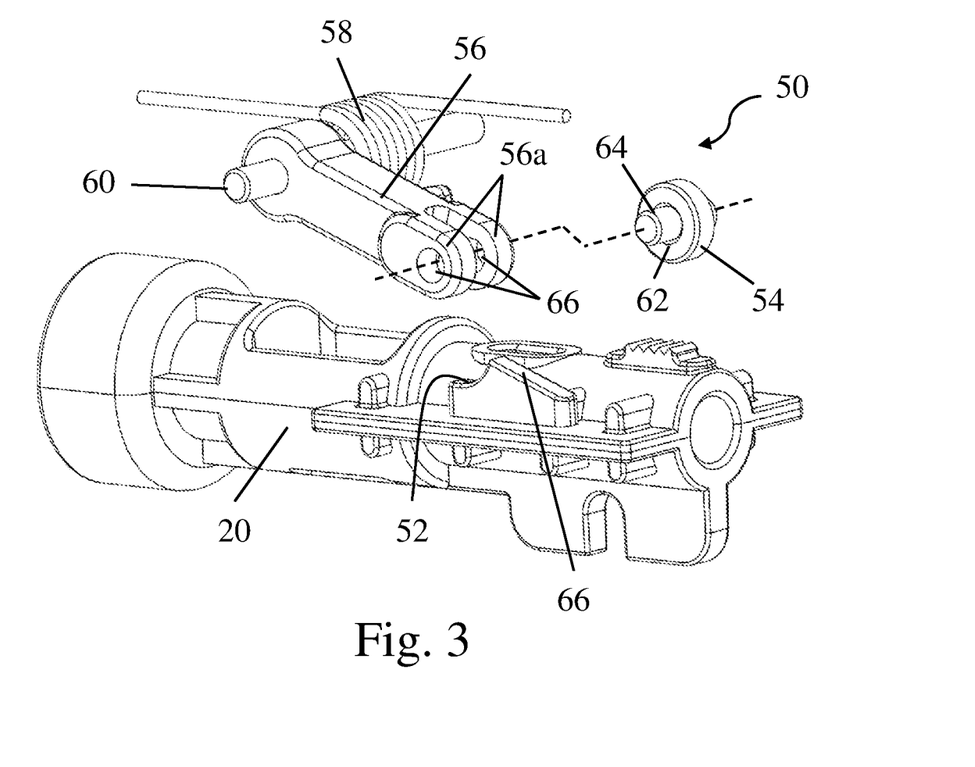
FIG. 3 is an exploded perspective view of the actuation lockout system of FIG. 2.

FIG. 1 depicts a surgical instrument 10 including a handle 12 and a hollow elongated shaft 14 extending from the handle towards a distal end of the device from which fasteners are deployed. The surgical instrument has a power transmission including a trigger 16, a transmission linkage 18, a shuttle 20, and a driveshaft 24. The trigger is coupled to the transmission linkage, which is operatively coupled to the shuttle, which is in turn coupled to the driveshaft. Thus, when the trigger is actuated, the transmission linkage displaces the shuttle and associated driveshaft in a distal direction. The driveshaft is configured and arranged to apply a force to a distally located fastener, either directly or indirectly, to deploy the fastener from the surgical instrument. When released, the trigger is returned to an initial position by a return spring 22. This, in turn, returns the shuttle and driveshaft to their initial positions. Thus, actuation of the trigger reciprocates the shuttle and driveshaft between distal and proximal positions. While a specific linkage and trigger mechanism are depicted in the figure, different triggers and transmission linkages are envisioned. For example, a transmission linkage may incorporate gears, multi-bar linkages, or any other appropriate transmission mechanisms. Also, in some embodiments, the transmission linkage, or other power transmission component, is constructed to provide a mechanical advantage for displacing the shuttle.

FIGS. 1-4 also illustrate an embodiment of an actuation lockout system 50 that may be included in a surgical instrument. In the depicted embodiment, the actuation lockout system includes a first camming surface 52 disposed on the shuttle 20, and a second camming surface 54 disposed on an arm 56. The arm is rotatable about an axle 60 associated with the handle 12. A biasing member 58 is operatively coupled to the arm. In the depicted embodiment, the biasing member is a torsion spring. However, other types of biasing members may be suitable, as described below. The biasing member biases the arm such that the second camming surface is urged toward the first camming surface. This arrangement resists the force applied to the second camming surface by the first camming surface when the shuttle is actuated by the trigger 16. This resistance to movement provides a threshold force which must be overcome to move the actuation lockout system from the locked configuration to the unlocked configuration. As the force applied to the trigger increases, the force applied to the second camming surface by the first camming surface also increases until it meets or exceeds the resisting force provided by the biasing member. Once the threshold force is met or exceeded, the first camming surface displaces the second camming surface to permit distal motion of the shuttle and the driveshaft.

Figure 4A:
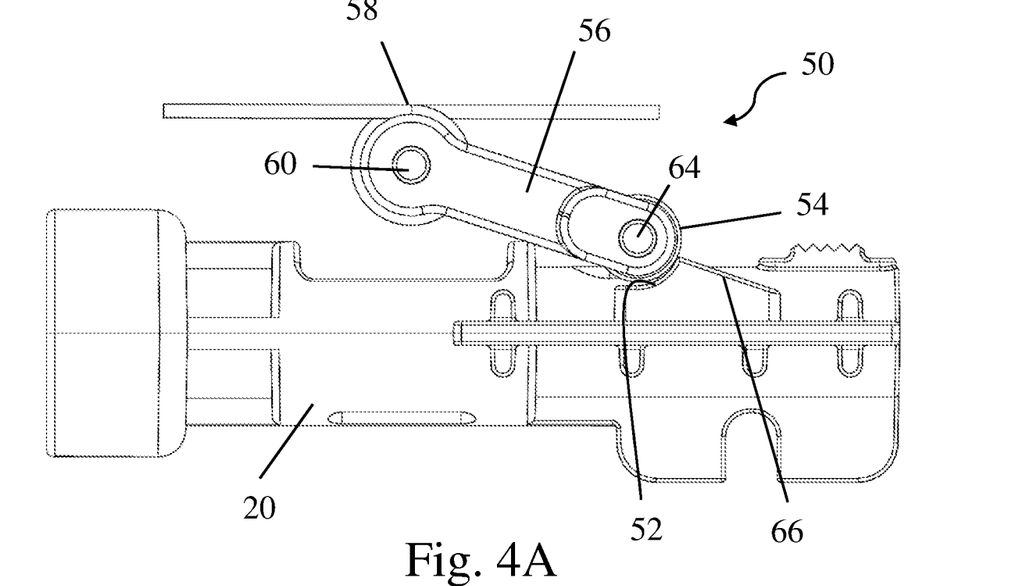
FIG. 4A is a side view of one embodiment of a surgical instrument incorporating an actuation lockout system in a locked configuration.
Figure 4B:
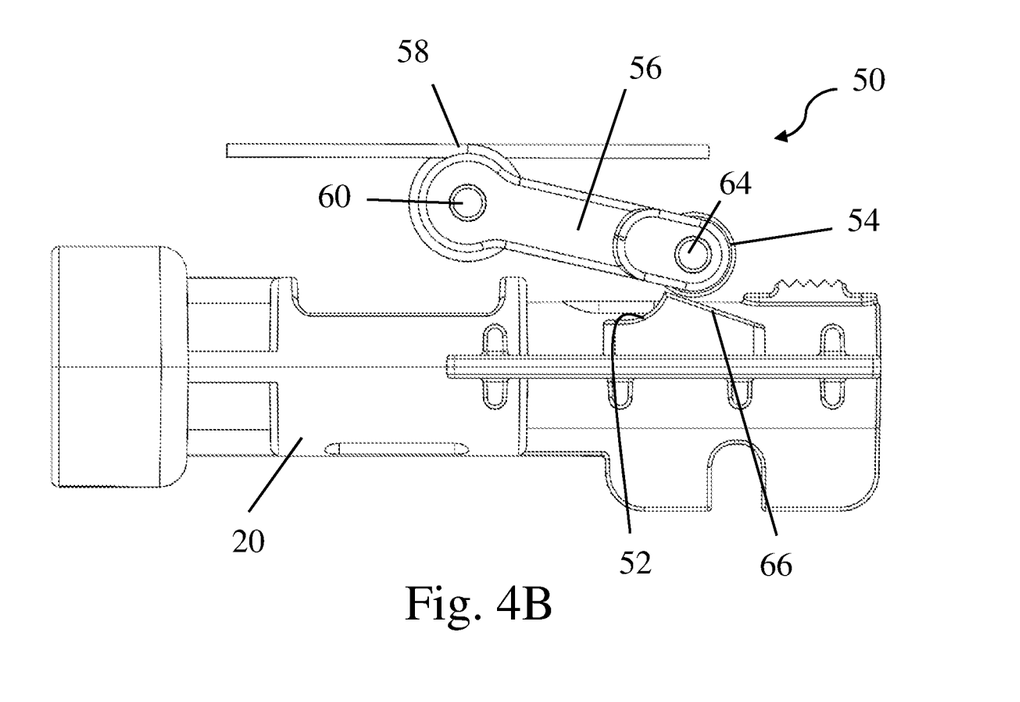
FIG. 4B is a side view the actuation lockout system of FIG. 4A in an unlocked configuration.

In view of the above, the actuation lockout system is movable between a locked configuration (FIG. 4A), and an unlocked configuration (FIG. 4B). In the locked configuration, the first and second camming surfaces are in contact with one another, thus restricting distal movement of the shuttle. In the unlocked configuration, the second camming surface has been cammed out of the path of travel of the first camming surface by an applied actuation force, thus removing the restraint from the shuttle, and permitting the shuttle and associated driveshaft to move distally to deploy a fastener, as described above. Although in the depicted embodiment, the first and second surfaces are disposed on the shuttle and the arm, respectively, other arrangements are envisioned. For example, the first and second camming surfaces may be disposed on any suitable part of the surgical instrument such as the handle, or on any part of the power transmission including the driveshaft, the transmission linkage, or the trigger.

Figure 4C:
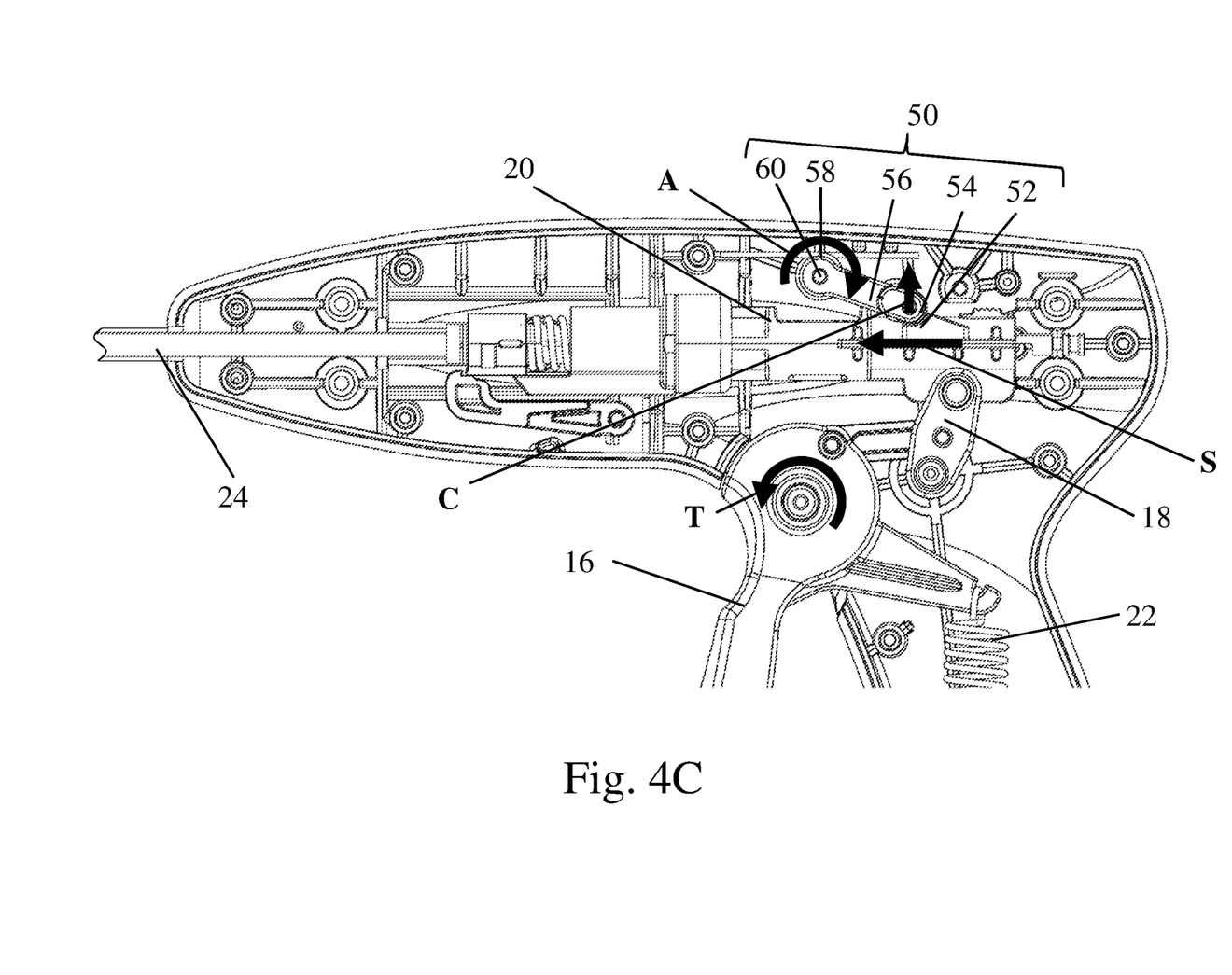
FIG. 4C is a cross-sectional view of a surgical instrument including the actuation lockout system of FIG. 4A during actuation.

As best illustrated by the embodiment depicted in FIG. 4C, the camming surfaces 52 and 54 may be configured such that distal movement of the shuttle 20 causes the first camming surface to apply a camming force C to the second camming surface in a direction transverse to both a longitudinal axis of the driveshaft and a direction of movement of the shuttle. This force displaces the second camming surface out of the path of movement of the first camming surface which places the actuation lockout system in the unlocked configuration. In the depicted embodiment, this displacement is embodied by rotation of the arm 56 about axle 60. While an embodiment has been described where an arm rotates to move to the unlocked position, it should be understood that the arm, or other appropriate locking member, may also be moved in any appropriate manner including linearly in response to interaction of the camming surfaces to selectively lock actuation of a surgical instrument. For example, a camming surface may be connected to a linearly expanding spring, such as a coil spring, such that it is displaced transverse to a path of movement of the corresponding camming surface instead of rotating out of the way.

It should be understood that camming surfaces used in an actuation lockout system may have any suitable shape and/or configuration. For example, in the depicted embodiment, the first camming surface is a concave curved surface formed on the shuttle 20. The curve may have any suitable radius, and the radius may be constant, or may be different along different points of the curve to provide a desired actuation force profile. Correspondingly, in some embodiments, the use of a rolling camming surface may be desirable to provide easier and/or smoother operation of the camming interface. One such embodiment is a cylindrical roller 62 as depicted in the figures. In the depicted embodiment, the radius of the roller generally complements the curvature of the first camming surface. However, embodiments in which the curvatures, or other shape, of the camming surfaces do not complement each other are also contemplated. The roller includes a through hole in which a roller axle 64 is received in through holes 66 formed in tabs 56a extending from arm 56. In some embodiments, the roller 62 may include bearings, such as ball bearings or roller bearings, to further facilitate rotation of the roller on the roller axle. Alternatively, a roller may not include a bearing, and may instead feature a suitable clearance around an axle to facilitate rotation. In other embodiments, the second camming surface 54 may not rotate, and instead may simply slide relative to the first camming surface 52. Furthermore, it should be understood that the first and/or second camming surfaces may not include any curvature; for example, flat angled camming surfaces may be suitable in some embodiments.

Having described the various components of a power transmission and actuation lockout system included in a surgical instrument, their method of operation is described in more detail with reference to FIGS. 4A-4C. FIGS. 4A and 4C depict the actuation lockout system in the locked configuration. The camming surfaces 52 and 54 are engaged to restrain distal motion of the shuttle 20 and associated driveshaft 24. Biasing member 58 biases arm 56 in direction A urging the camming surfaces together, as described above. When a force is applied to trigger 16, rotation of the trigger in direction T applies a force to the shuttle 20 via linkage 18 in a distally oriented direction S. The force in direction S then produces a camming force on arm 56 in direction C away from the path of movement of the shuttle due to the camming arrangement of surfaces 52 and 54. While another force component is also applied in the distal direction by the camming arrangement, this component of the applied force has not been illustrated in the figure for clarity. As depicted in FIG. 4C, the camming force applied in direction C to the second camming surface opposes at least a portion of the force applied by the biasing member in rotational direction A. When the force applied to the trigger exceeds a threshold force, the force along direction C is equal to or greater than the opposing force applied by the biasing member. Once this occurs, the second camming surface is displaced out of the path of the shuttle and first camming surface placing the actuation lockout system in the unlocked configuration, as shown in FIG. 4B. In the unlocked configuration, the shuttle 20 and driveshaft 24 are displaced distally along direction S in order to deploy a surgical fastener, as described above.

In the depicted embodiment, the shuttle 20 further includes a surface 66 on which the second camming surface 54 travels when the actuation lockout system 50 is in the unlocked configuration. Specifically, surface 66 includes a slope which allows the force in the biasing member 58 to decrease as the shuttle moves distally. The slope of the surface may be chosen such that the force provided by return spring 22 is sufficient to urge the actuation lockout system back into the locked configuration after a surgical fastener is deployed and a force applied by a user to the trigger 16 is removed. In some embodiments, the surface may act as a third camming surface which interacts with the second camming surface to provide additional force to the shuttle or driveshaft in the distally oriented direction S due to the force applied by the biasing member. Such a configuration may further promote complete actuation of the surgical instrument when the actuation lockout system moves from the locked configuration to the unlocked configuration. However, it should be understood that surface 66 may simply be flat, may not act as a camming surface, may be curved, or have any other suitable shape and/or configuration for accommodating the second camming surface as the shuttle is displaced, as the disclosure is not so limited.

While the first camming surface has been depicted on the shuttle, the current disclosure of an actuation lockout system is not so limited. Therefore, it should be understood the first camming surface may be disposed on the driveshaft, a component coupled to the driveshaft, the trigger, or any other appropriate portion of the power transmission system such that actuation of the trigger displaces the camming surfaces relative to each other to selectively permit actuation of the driveshaft once a threshold force has been applied to the trigger. For example, in one embodiment, a camming surface may be arranged coaxially with the driveshaft. Furthermore, although in the depicted embodiment, the actuation lockout system is disposed on one side of the shuttle, in other embodiments, portions of an actuation lockout system may be provided on either or both sides of the shuttle, or it may not be associated with the shuttle at all.

Although the use of complementary camming surfaces is depicted in the figures to move the actuation lockout system from the locked configuration to the unlocked configuration, other arrangements and mechanisms are also contemplated. For example, the actuation lockout system may include a rack and pinion arrangement such as a pinion gear coupled to the trigger and rack formed on surface arranged to limit actuation. Actuation of the trigger may rotate the pinion and in turn drive a displacement of the rack and the associated surface towards the unlocked configuration. Alternatively, linkages coupled to the trigger may be arranged to displace a locking mechanism. In another example, a camming surface may be disposed on ratchet and pawl arrangement which selectively locks the actuation lockout system. The camming surface may move the pawl over a tooth or similar feature on the ratchet when a threshold force is applied to the camming surface in order to move the ratchet and pawl to an unlocked configuration. In further examples, an actuation lockout system may include complementary surfaces which may be selectively engaged to form an interference fit, a latch which is configured to release above a predetermined threshold force, or any other suitable mechanism or arrangement, as the disclosure is not so limited. A locking mechanism may include a catch, latch, clasp, a deadbolt, a hook and eye, or any other suitable arrangement. An interference fit between complementary surfaces may provide a frictional resistance force; the resistance force may provide the threshold force which must be overcome to move the actuation lockout system to the unlocked configuration. In view of the above, it should be understood that an actuation lockout system may include any suitable arrangement of components which restricts relative motion of two or more components along at least one direction when in a locked configuration. Furthermore, an actuation lockout system may include any suitable mechanism to move the actuation lockout system between the locked and unlocked configurations; such mechanisms may or may not be coupled to a trigger of a surgical instrument.

As described above, in some embodiments, an actuation lockout system includes a biasing member coupled to at least one camming surface to apply a locking force and selectively prevent actuation of the surgical instrument. However, it should be understood that embodiments that do not include a biasing member are also contemplated as the disclosure is not so limited. For example, a frictional interface, a particular shape and/or configuration of surfaces, or any other suitable arrangement may be used to provide a threshold actuation force for unlocking the actuation lockout system as the disclosure is not so limited.

While a torsion spring has been illustrated for the biasing member, the biasing member is not limited to only a torsion spring. For example, the biasing member may include, but is not limited to, a coil spring, a leaf spring, a magazine spring, a gas spring, an elastic rod, or any other suitable structure or device capable of providing a force to resist displacement of the second camming surface and provide a threshold force for selectively unlocking the actuation lockout system. Additionally, while a separate biasing member has been depicted, a biasing member may also be integrally formed with a portion of the actuation lockout system. For example, an integrally formed feature such as a flexible arm, tab, or other feature may function as both a camming surface and biasing member as the disclosure is not so limited.

In certain embodiments, an actuation lockout may be particularly useful when incorporated in a surgical instrument with a power assist device configured to aid in deploying a surgical fastener. The power assist device may be configured to provide a short duration impulse to the driveshaft by striking the driveshaft with a moving mass, as described in more detail below. Without wishing to be bound by theory, providing a short duration impulse may result in a larger force being applied to a fastener during deployment, which may improve prosthetic fabric penetration and reduce the required manual force input from a user. Depending on the particular embodiment, a power assist device may be actuated when a threshold force is applied to the trigger and an actuation lockout system is moved from a locked configuration to an unlocked configuration.

Figure 5:
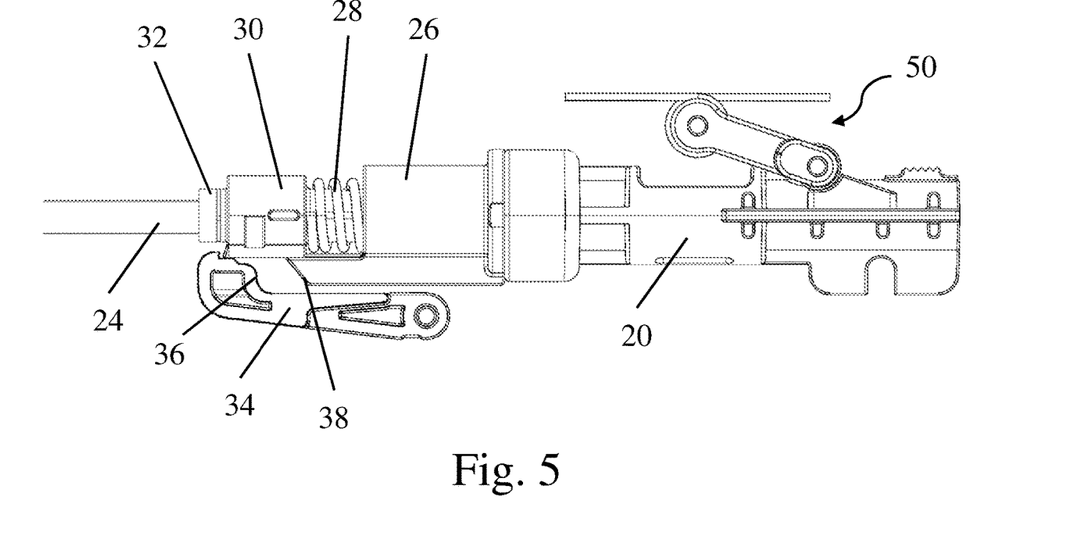
FIG. 5 is a side view of one embodiment of an actuation lockout system and a power assist device associated with a driveshaft.

One embodiment of a power assist device is depicted in FIGS. 1 and 5. The depicted power assist device includes an energy storage member 28, a striker 30, and an impact surface 32. In the depicted embodiment, the impact surface 32 is a collar coupled to the driveshaft 24, though other arrangements are also contemplated. The power assist device also includes an energy storage member housing 26 and a locking mechanism 34. As depicted in the figures, the energy storage member is a coil spring. However, the energy storage member may be any appropriate component capable of storing and releasing energy including coil springs, air springs, gas springs, elastic rods or bands, magazine springs, leaf springs, torsion bars, or torsion springs. Further, the energy storage member housing is operatively coupled to the shuttle 20. The energy storage member is coaxially disposed on the driveshaft 24 and partially disposed within an interior volume of the energy storage member housing. However, other configurations including ones where the energy storage member is disposed outside of the housing are also contemplated. The energy storage member and energy storage member housing are configured such that displacing the driveshaft in the distal direction displaces the energy storage member housing and associated proximal end of the energy storage member in the distal direction as well. Since the energy storage member 28 is located between the striker and energy storage member housing while the striker is locked in place by the locking mechanism 34, this movement compresses the energy storage member.

As the driveshaft continues to be displaced in the distal direction, the locking mechanism 34 is moved to the unlocked position through the use of a first power assist camming surface 38 located on the energy storage member housing 26 and a second power assist camming surface 36 located on the locking mechanism. As the energy storage member housing 26 is displaced in the distal direction, the first power assist camming surface comes into contact with the second power assist camming surface and displaces the locking mechanism outwards to release the striker 30 and the energy storage member 28. The released energy storage member accelerates the striker in the distal direction towards the impact surface 32 to impart an impulse to the driveshaft 24 and deploy an associated fastener. Upon being struck, the driveshaft accelerates in a distal direction to deploy a fastener.

While one particular power assist device has been described herein, other suitable embodiments, arrangements, and/or configurations of a power assist device for use in a surgical instrument are also described in U.S. patent application Ser. No. 13/804,043 filed on Mar. 14, 2013, published as US 2014/0276963, the disclosure of which is hereby incorporated by reference in its entirety.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A method of operating a surgical instrument, the method comprising:
   blocking movement of a first camming surface associated with a portion of a power transmission with a second camming surface in a locked configuration to prevent movement of a driveshaft operatively coupled with the power transmission;
   permitting movement of the first camming surface with the second camming surface when the second camming surface is in an unlocked configuration to permit movement of the driveshaft; and
   applying a distally directed force to a third camming surface associated with the driveshaft with the second camming surface when the second camming surface is in the unlocked configuration.

2. The method of claim 1, wherein the second camming surface is associated with a handle of the surgical instrument.

3. The method of claim 1, wherein at least one of the first camming surface and the second camming surface includes at least a portion of a rotatable arm.

4. The method of claim 1, wherein at least one of the first camming surface and the second camming surface includes a roller.

5. The method of claim 4, wherein the second camming surface includes the roller, the roller comprising a cylindrical roller.

6. The method of claim 1, wherein at least one of the first camming surface and the second camming surface has a curved shape.

7. The method of claim 6, wherein the first camming surface has a concave curved shape.

8. The method of claim 1, further comprising biasing at least one of the first camming surface and the second camming surface towards the locked configuration.

9. A method of operating a surgical instrument, the method comprising:
   biasing a second camming surface against a first camming surface to block movement of the first camming surface with the second camming surface in a locked configuration to prevent movement of a driveshaft operatively coupled to the first camming surface, wherein the first camming surface has a curved shape and the second camming surface includes a roller; and
   permitting movement of the first camming surface when the second camming surface is in an unlocked configuration to permit movement of the driveshaft.

10. The method of claim 9, further comprising applying a distally directed force to a third camming surface associated with the driveshaft with the second camming surface when the second camming surface is biased against the third camming surface in the unlocked configuration.

11. The method of claim 10, wherein the third camming surface slopes towards a proximal end of the driveshaft.

12. The method of claim 9, wherein the second camming surface is associated with a handle of the surgical instrument.

13. The method of claim 9, wherein the roller of the second camming surface is connected to a rotatable arm.

14. The method of claim 13, further comprising rotating the rotatable arm between the locked configuration and the unlocked configuration.

15. The method of claim 9, further comprising biasing the second camming surface towards the first camming surface with a biasing member operatively coupled to the second camming surface.

16. The method of claim 9, wherein the first camming surface and the roller have complementary shapes.

17. A method of operating a surgical instrument, the method comprising:
 camming a second camming surface out of contact with a first camming surface associated with a driveshaft to permit movement of the driveshaft;
 camming the second camming surface against a third camming surface associated with the driveshaft, wherein the third camming surface is located proximally relative to the first camming surface, and wherein the third camming surface slopes towards a proximal end of the driveshaft.

18. The method of claim 17, further comprising applying a distally directed force to the third camming surface with the second camming surface when the second camming surface is cammed against the third camming surface.

19. The method of claim 17, wherein the second camming surface includes a roller, and the first camming surface has a curved shape.

20. The method of claim 19, wherein the roller of the second camming surface is connected to a rotatable arm.

21. The method of claim 17, further comprising biasing the second camming surface towards the first camming surface and the third camming surface as the driveshaft moves from a first position to a second position.

* * * * *